(12) United States Patent
Skaggs

(10) Patent No.: US 7,319,230 B2
(45) Date of Patent: Jan. 15, 2008

(54) DISINFECTION AND DECONTAMINATION USING ULTRAVIOLET LIGHT

(76) Inventor: Donald E. Skaggs, 861 Burkewood Dr., Lexington, KY (US) 40509

( * ) Notice: Subject to any disclaimer, the term of this patent is extended or adjusted under 35 U.S.C. 154(b) by 244 days.

(21) Appl. No.: 11/181,502

(22) Filed: Jul. 14, 2005

(65) Prior Publication Data

US 2006/0011856 A1  Jan. 19, 2006

Related U.S. Application Data

(60) Provisional application No. 60/587,859, filed on Jul. 15, 2004.

(51) Int. Cl.
  *G01N 23/00* (2006.01)
  *A61L 2/10* (2006.01)
  *B01D 50/00* (2006.01)

(52) U.S. Cl. ............... 250/455.11; 250/461.1; 250/494.1; 250/504 R; 422/1; 422/22; 422/24; 422/28; 96/224; 210/748; 210/764

(58) Field of Classification Search ............ 250/455.11
  See application file for complete search history.

(56) References Cited

U.S. PATENT DOCUMENTS

| | | | | |
|---|---|---|---|---|
| 4,871,559 A * | 10/1989 | Dunn et al. ............... 426/248 |
| 4,907,316 A * | 3/1990 | Kurz ......................... 15/319 |
| 6,383,177 B1 * | 5/2002 | Balle-Petersen et al. ....... 606/9 |
| 6,403,033 B1 * | 6/2002 | Gutman ..................... 422/29 |
| 6,468,433 B1 * | 10/2002 | Tribelski ................... 210/748 |
| 6,524,529 B1 * | 2/2003 | Horton, III ................ 422/24 |
| 6,776,824 B2 * | 8/2004 | Wen ......................... 96/223 |
| 6,811,748 B2 * | 11/2004 | Ettlinger et al. ............ 422/24 |
| 2002/0033369 A1 * | 3/2002 | Bender ..................... 210/748 |
| 2002/0122743 A1 * | 9/2002 | Huang ...................... 422/24 |
| 2005/0000365 A1 * | 1/2005 | Nelsen et al. .............. 96/224 |
| 2005/0079096 A1 * | 4/2005 | Brown-Skrobot et al. .... 422/24 |
| 2006/0011856 A1 * | 1/2006 | Skaggs ................. 250/455.11 |
| 2006/0133950 A1 * | 6/2006 | Teppke ..................... 422/28 |
| 2006/0156753 A1 * | 7/2006 | Fuhr et al. .................. 62/378 |
| 2006/0278088 A1 * | 12/2006 | Helsel ....................... 96/224 |

* cited by examiner

*Primary Examiner*—David A. Vanore
*Assistant Examiner*—Bernard Souw
(74) *Attorney, Agent, or Firm*—King + Schickli, PLLC

(57) ABSTRACT

An apparatus and method for disinfecting a cryostat is provided. The cryostat disinfecting device comprises an ultraviolet emitter, a pulsed power control system, a mirrored cover and a safety shield. The device is lowered into a cryostat chamber and produces high intensity pulsed UV energy, disinfecting the cryostat chamber. After disinfection, the device is removed from the cryostat for storage or use on another cryostat. This provides mobility and access for disinfecting cryostats under continuous daily use conditions, and reduces the exposure risk of biological and chemical hazards to the operator.

21 Claims, 6 Drawing Sheets

TOP PERSPECTIVE VIEW

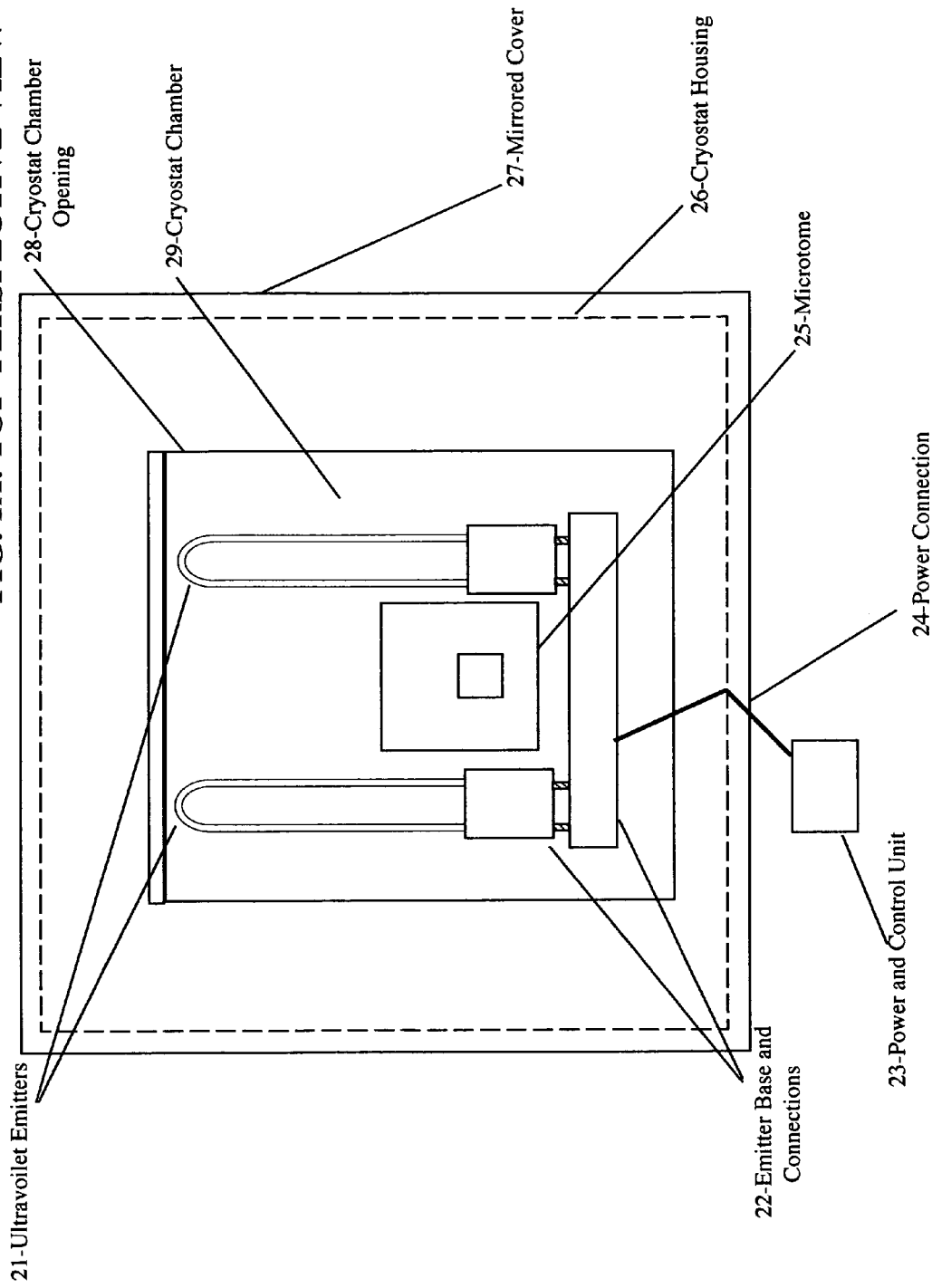

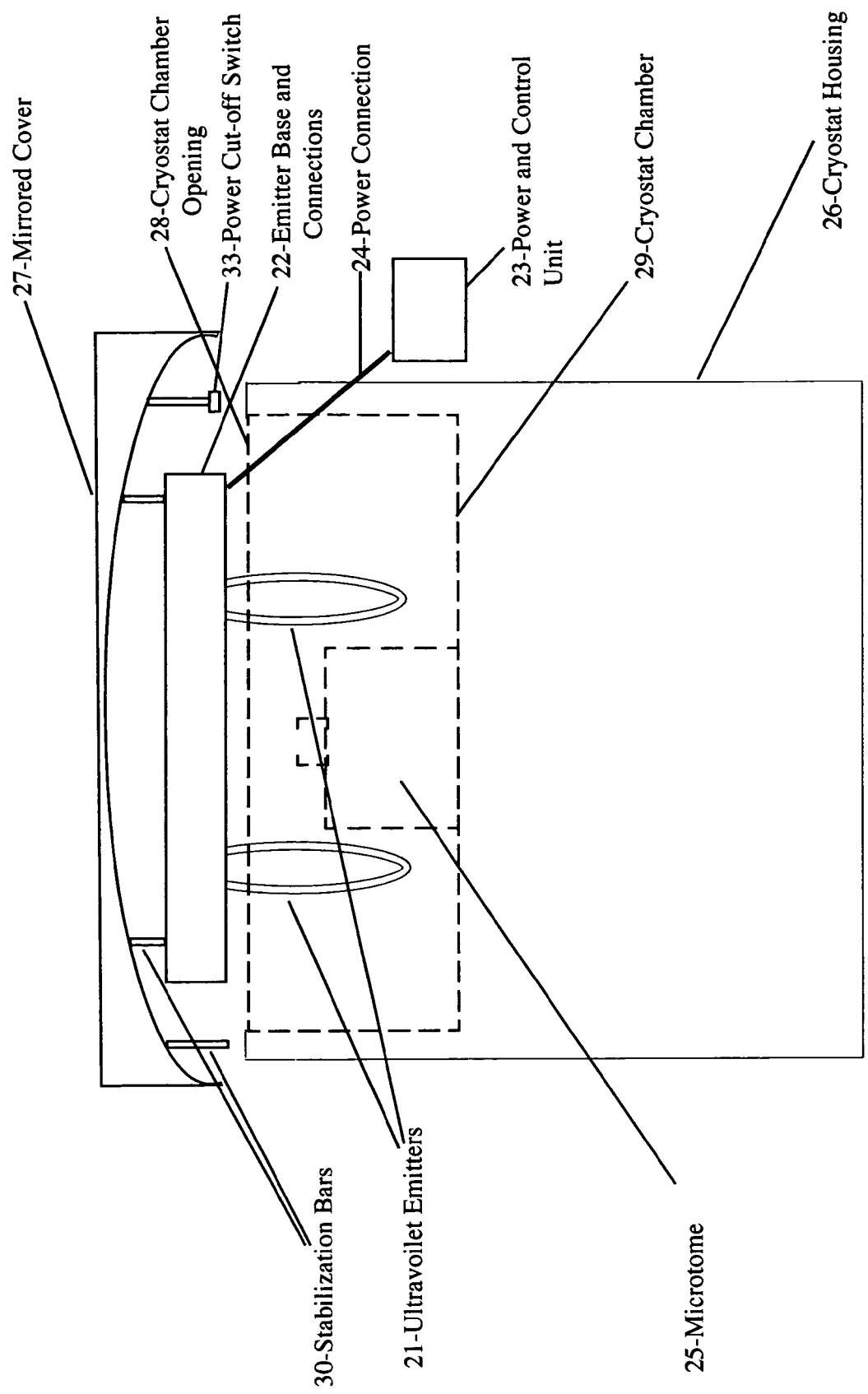
FIG. 1B: FRONT PERSPECTIVE VIEW

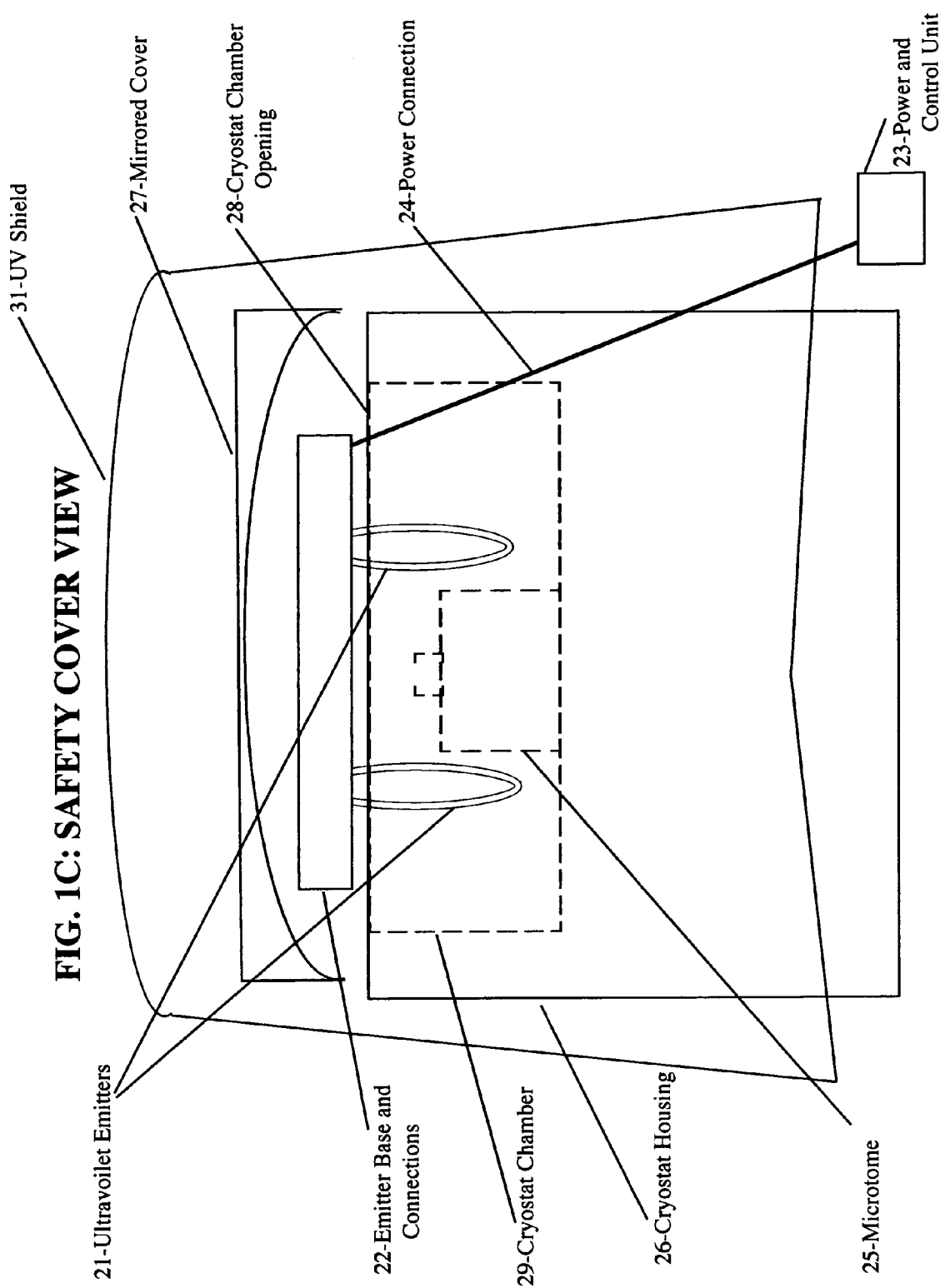

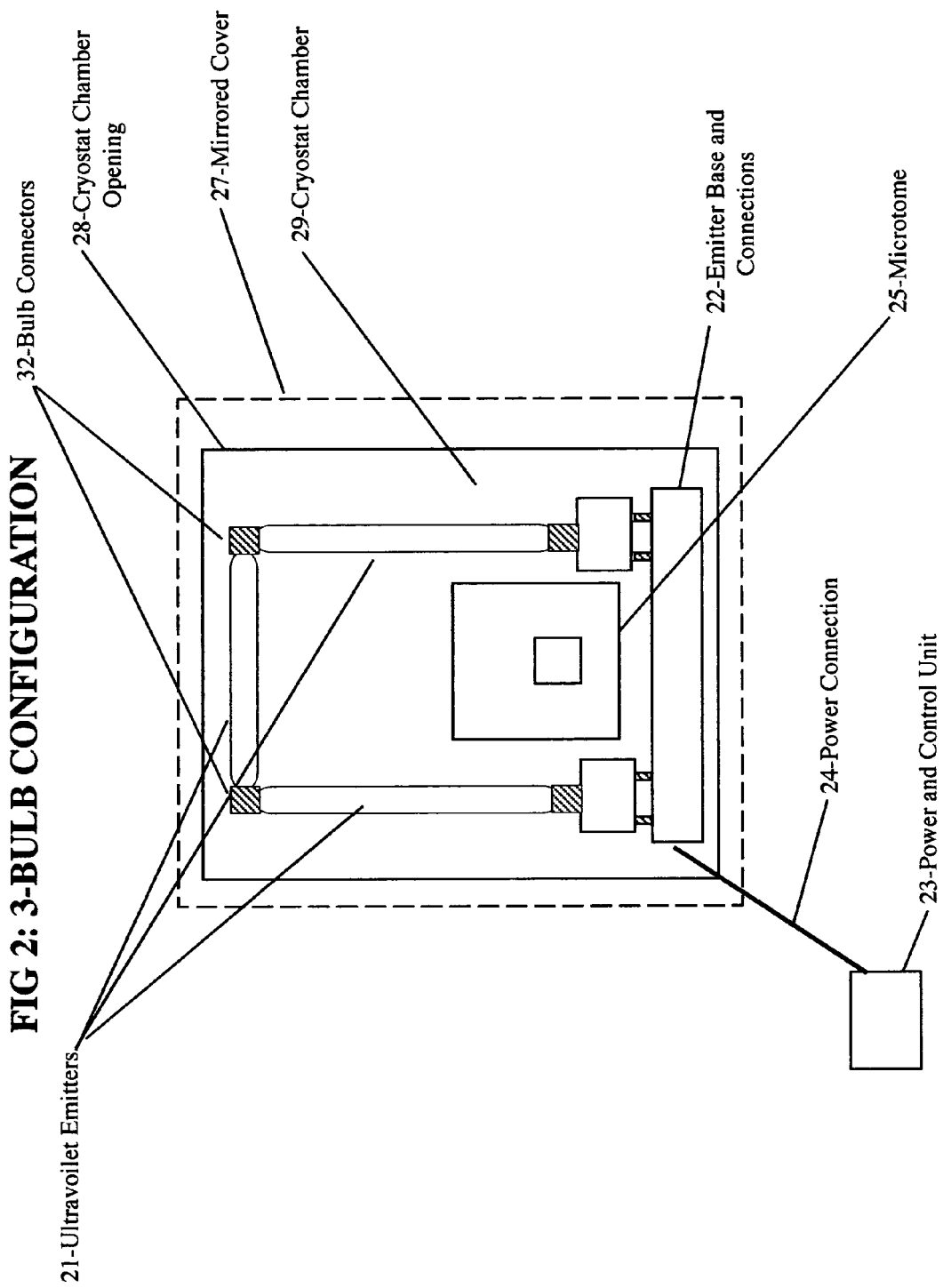

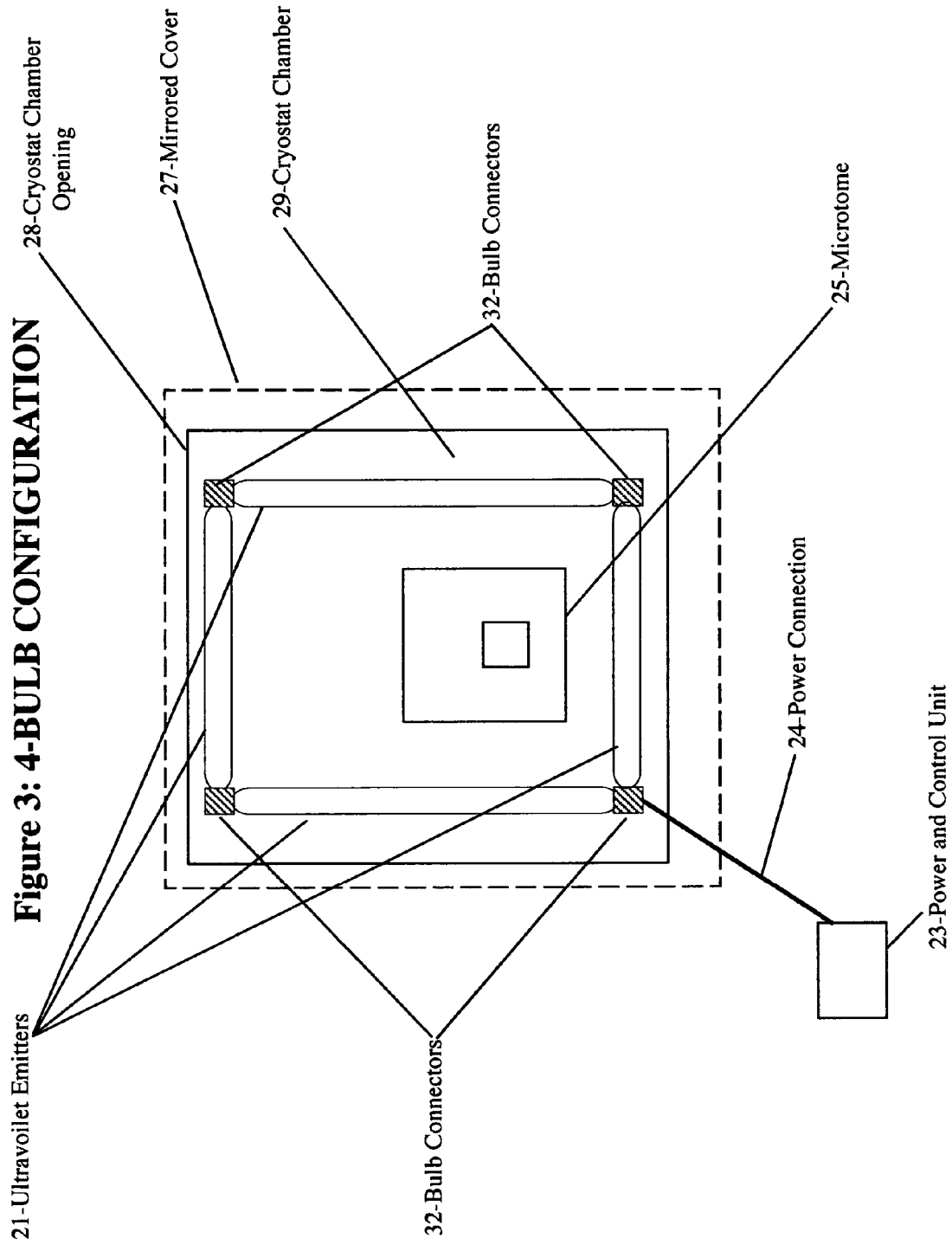

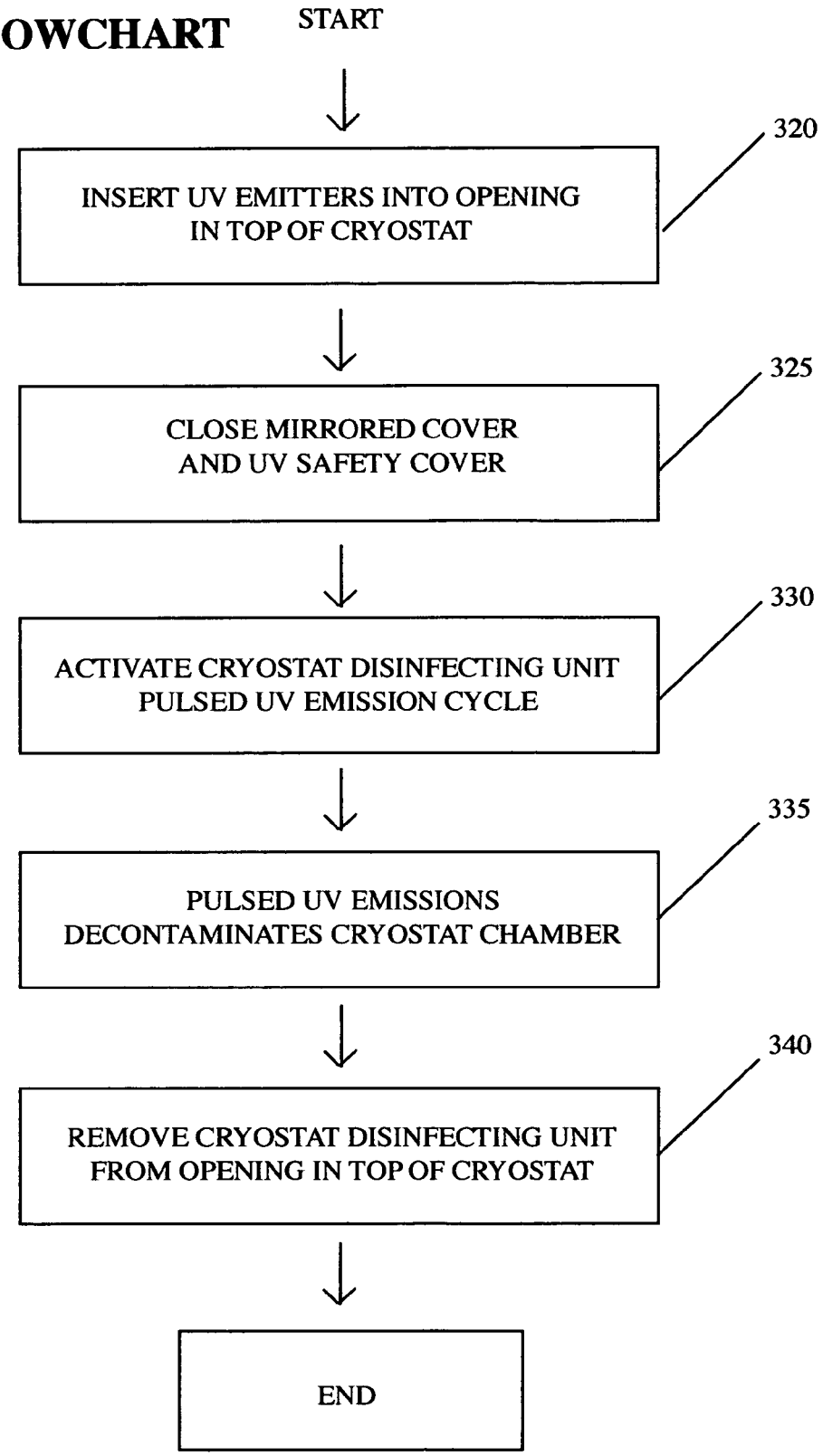

DISINFECTION AND DECONTAMINATION USING ULTRAVIOLET LIGHT

CROSS REFERENCE TO RELATED APPLICATIONS

This application claims the benefit of PPA Ser. No. 60/587,859, filed Jul. 15, 2004 by the present inventor.

Other References

1. Cryostat Decontamination, Posting on Histonet, Mar. 4, 2000 http://www.histosearch.com/histonet/Mar00/Re-.cryostatdecontaminatio.html by Tim Morken, Infectious Disease Pathology, Centers for Disease Control.
2. UV Curing Technical Data, Honovia Corp., Union, N.J.
3. Germicidal and Short Wave UV Radiation, Sylvania-Engineering Bulletin, #0-342
4. Air Disinfection Technical Data, Miltec UV, Stevensville, Md.
5. UV Disinfection Technical Data, Ushio America, Inc., Cypress, Calif.
6. Photochemical Sterilization by Pulsed Light, Technical Data, Xenon Corporation, Woburn Mass.
7. U.S. Pat. No. 6,481,219 (2002) to Palermo

FEDERALLY SPONSERED RESEARCH

Not Applicable

SEQUENCE LISTING OR PROGRAM

Not Applicable

BACKGROUND OF THE INVENTION—FIELD OF INVENTION

This invention relates to the disinfection of biologically contaminated laboratory equipment, specifically cryostat chambers using an improved ultraviolet light-emitting device.

BACKGROUND OF THE INVENTION

Cryostats are essentially devices that contain a bladed microtome inside of a cryogenic chamber. Biological tissue samples are embedded in a matrix and quickly frozen within the cryostat, which then can be sliced by an internal microtome into a section thin enough to be placed on a microscope slide. The slide is then promptly stained and reviewed by microscopic examination.

Commonly used in the health care industry to freeze biological samples for prompt pathological analysis, cryostat chambers are in a constant low-temperature state. In a routine health care environment, cryostats receive multiple biological tissue samples from a variety of sources throughout an average workday. Standard procedure dictates that the cryostat be periodically cleaned and disinfected to reduce contamination between individual samples and to lower exposure and infection risk to laboratory personnel. Many busy laboratories cannot feasibly take the time necessary for currently effective methods required to disinfect the chamber between each sample. Currently used methods have required the operator to decontaminate and disinfect the unit by first defrosting the unit, then hand-washing the chamber with a liquid cleaner or disinfectant such as alcohol, formaldehyde and/or glutaraldehyde solutions, or expose the defrosted unit to disinfecting gasses. Below are some common specific examples of current recommended procedures for decontaminating cryostats.

In many of these cases the cryostat must be defrosted before decontamination:

(1) Washing out with 100% alcohol
(2) Washing out with 10% formaldehyde, 2% glutaraldehyde or other harsh chemical solution followed by water wash, followed by 100% alcohol.
(3) Placing a dish of 37% (concentrated) formaldehyde in cryostat chamber and leaving overnight.
(4) Exposing the cryostat chamber to high concentrations of ozone, an unstable and potentially hazardous chemical with a history of breaking down materials and surfaces it comes into contact with.

In a small percentage of newer cryostat models, attempts have been made to design the cryostat as "self-cleaning", through the use of automatic systems that mimic some of the cleaning procedures listed above, for example, U.S. Pat. No. 6,481,219 (2002) to Palermo. However, most cost-conscious health care facilities consider a cryostat a major capitol purchase, resulting in the majority of cryostats in use for the next several decades to be standard models with no automatic cleaning cycles.

These disadvantages, along with the unfeasibility for many facilities to take the time involved in allowing the cryostat to defrost for disinfection and re-cool for the next specimen, make disinfecting most cryostat units less frequent, and subsequently increases the risks of both chemical and biohazard exposure to the operator.

Ultraviolet (UV) disinfection is a proven effective means of surface sterilization, air and water purification, sewage treatment, protection of food and beverages, and many other applications. UV is capable of disinfecting water faster than chlorine without the use of harmful chemicals. However, in the cryostat disinfection setting, the use of standard continuous UV bulb exposure can be problematic. While ultimately effective, the length of time necessary to effect disinfection using standard continuous UV can produce ozone, a chemical that is toxic to humans when inhaled in high concentrations.

Accordingly, there is a need for a device and method to disinfect and decontaminate the large percentage of multiple, older, standard and non-self-cleaning cryostats using an effective ultraviolet light in the disinfecting spectrum and frequency known to kill pathogens, while reducing the potential risk of exposing the operator to biological and chemical hazards. Current methods in use for decontamination of cryostats suffer from a number of disadvantages:

(a) Most cryostats currently in use have no disinfection systems built in.
(b) Cryostats that have disinfection systems built in use harsh chemicals and gasses such as formaldehyde, glutaraldehyde, paracetic acid and ozone.
(c) The majority of cryostats require lengthy defrost and re-cooling cycles to effect decontamination procedures involving chemicals.
(d) Low efficiency, standard continuous UV lamp exposure inactivates microbes at a low rate over an extended period of time, potentially producing harmful ozone exposure levels.
(e) Efficient, pulsed UV emitting systems currently in use are not mobile and cannot be inserted into the configuration of a cryostat.

BACKGROUND OF INVENTION—OBJECTS AND ADVANTAGES

In addition to the overall effectiveness of UV light, pulsed UV light inactivates microbes with a rapidity and effectiveness not found with standard continuous UV bulb exposure. Only a few pulses are sufficient to completely eradicate microorganisms and provide a much higher rate of disinfection than standard continuous UV light exposure. Since microorganisms encompass four major groups (viruses, bacteria, fungi and protozoa), each group has individual cells, which require different levels of UV energy for destruction. High intensity short-pulsed UV exposure can accomplish all these levels with the same number of microwatt seconds per square centimeter.

Accordingly, besides the objects and advantages of the mobile, pulsed UV emitter described in the patent, several objects and advantages of the present invention are:

(a) to provide a UV emitter which can be produced or adjusted in a variety of arrays to maximize exposure of surface areas in all types, configurations and models of cryostats.

(b) to provide a UV emitter which is a mobile unit, independent of the cryostat and can be used on multiple cryostats in a single health care facility.

(c) to provide a UV emitter which can be used in older and standard model cryostats with no automatic cleaning cycles.

(d) to provide a UV emitter which will provide high intensity short-pulsed UV exposure at all levels required for the destruction of all microorganism types and cell structures.

(e) to provide a UV emitter which can be inserted into a continuously cold-running cryostat between specimen sample submissions, without taking the lengthy time required for defrosting and re-cooling.

(f) to provide a UV emitter which will reduce the exposure of the cryostat operator to both biological and chemical hazards.

(g) to provide a UV emitter whose pulsed UV design will inactivate microorganisms at a much faster rate than standard continuous UV lamp exposure.

Still further objects and advantages will become apparent from a consideration of the ensuing description and drawings.

SUMMARY

In accordance with the present invention an ultraviolet light emitting device comprises an emitter or array of emitters connected to a power and control unit, that are independent of and inserted into the cryostat device, providing a high intensity short-pulsed ultraviolet emission required to disinfect the interior of the cryostat chamber.

DRAWINGS—FIGURES

In the drawings, closely related figures have the same number but different alphabetic suffixes.

FIG. 1A shows a perspective of the top side of a cryostat with the UV emitters of the cryostat disinfecting unit (CDU) lowered into the cryostat chamber as one embodiment of the present invention.

FIG. 1B shows a perspective of the front-side of a cryostat with the UV emitters of the CDU lowered into the cryostat chamber as one embodiment of the present invention.

FIG. 1C shows a perspective of the front-side view of the configuration shown in FIG. 2, with the inclusion of a light shield covering the cryostat as another embodiment of the present invention.

FIG. 2 shows a top view perspective of a cryostat with the emitters of the CDU in a 3-Bulb emitter configuration lowered into the chamber as another embodiment of the present invention.

FIG. 3 shows a top view perspective of a cryostat with the emitters of the CDU in a 4-Bulb emitter configuration lowered into the chamber as another embodiment of the present invention.

FIG. 4 is a flowchart illustrating one method of performing any one of the embodiments illustrated in FIGS. 1-3.

| DRAWINGS-Reference Numerals | |
|---|---|
| 21 | ultraviolet emitters |
| 22 | emitter base and connections |
| 23 | power and control unit |
| 24 | power connection |
| 25 | microtome |
| 26 | cryostat housing |
| 27 | mirrored cover |
| 28 | cryostat chamber opening |
| 29 | cryostat chamber |
| 30 | stabilization bars |
| 31 | uv shield |
| 32 | bulb connectors |
| 33 | power cut-off switch |

DETAILED DESCRIPTION

In the following paragraphs, the present invention will be described in detail by way of example with reference to the attached drawings. Throughout this description, the preferred embodiment and examples shown should be considered as exemplars, rather than as limitations on the present invention. As used herein, "the present invention" refers to any of the embodiments of the invention described herein.

The present invention alleviates to a great extent the disadvantages of known apparatus and methods for disinfecting cryostats by providing a mobile emitter that disinfects using high intensity pulsed ultraviolet energy. In general, the present invention includes an ultraviolet (UV) light emitter connected to a base, power connectors and a power control unit that contains a pulsed electrical driver system. The UV emitter is lowered into the opening in the top of the cryostat chamber. The pulsed electrical control system sends pulsed UV energy into the cryostat chamber via the emitters, decontaminating all surfaces by causing photolysis, loss of colony-forming ability (death of microorganism), and inability to support phage growth (enzyme inactivation) and destruction of nucleic acid. This breaking down of organic molecular bonds results in molecular rearrangements and dissociation of the microbe's DNA with cellular damage, which inhibits reproduction. After the decontamination cycle is complete, the emitters are raised out of the cryostat chamber, and the disinfecting unit can be stored for later use or used on another cryostat needing decontamination.

Alternatively, the pulsed UV disinfecting unit can also be employed to disinfect other contaminated equipment used in the laboratory.

One aspect of the present invention is a safety feature in the form of UV light shield that can add an extra layer of protection to the operator from accidental exposure to the UV rays.

The present invention also provides a method for decontaminating the cryostat chamber that includes the steps of: (1) reflecting the pulsed UV rays that are emitting away from the chamber area via a mirrored cover stationed over the opening of the cryostat chamber; (2) putting the UV emitters into a motion sequence while in the cryostat chamber, maximizing the UV coverage areas; (3) removing the visible debris from the cryostat chamber with a biohazard-safe filtering vacuum prior to the insertion of the UV emitters; and (4) the use of an adjustable cycle timer within the power control unit to change the amount of timed energy required for individual efficacy needs.

Referring to FIGS. 1A, 1B and 1C, the present invention comprises an array of UV emitters 21 having a connection to a base 22 with a power connection 24 to a power control unit 23. The UV emitters 21 are lowered into the cryostat chamber 29 through the cryostat chamber opening 28 located at the top of the cryostat housing 26. The UV emitters 21 are positioned to allow the maximum coverage of UV radiation to the surfaces of the cryostat chamber 29 and enclosed microtome 25.

The power and control unit 23 causes the UV emitters 21 to generate a cycle of high intensity short-pulsed UV radiation in sufficient wavelengths and quantities to inactivate microorganisms on the exposed surfaces of the cryostat chamber 29 and microtome 25. Proteins and nucleic acid, which all microorganisms contain as their main constituents, absorb ultraviolet (UV) radiation energy. After absorption, the UV energy destroys or inactivates the DNA (deoxyribonucleic acid). The light energy absorbed causes both electronic and photochemical reactions. Unlike ordinary photolysis by continuous UV exposure, the excited or reactive species produced by pulsed UV light are in rather large concentrations. This absorbed energy causes the formation of Pyrinidone dimers in DNA, which leads to genetic damage to cells and their ultimate destruction. One aspect of the present invention is the use of a mirrored cover 27 strategically placed over the cryostat chamber opening 28. This will allow UV rays to be reflected back into the cryostat chamber 29 and on the microtome 25, further intensifying the disinfecting energy on these surfaces.

Referring to FIG. 1B, stabilization bars 30 are used to secure the disinfecting unit when mounted on the top of the cryostat housing 26 and over the cryostat chamber opening 28. A safety feature integrated into the stabilization bars is a power cut-off switch 33, preventing accidental emissions of UV light while a cover is not in place over the UV emitters 21.

Referring to FIG. 1C, the UV emitters 21 includes a UV protecting shield 31, placed over the mirrored cover 27, cryostat chamber opening 28 and UV emitters 21. The UV shield 31 would protect the operator from exposure to the UV rays from the emitters. A safety feature included in the power control unit 23 is that when the UV shield 31 or the mirrored cover 27 is lifted from the cryostat housing 26, the UV emitters will not operate, thereby preventing UV exposure to an operator.

Referring to FIG. 2, an alternative embodiment of the present invention is illustrated, which employs 3 UV emitters 21 that will add to the surface coverage areas of the cryostat chamber 29 and microtome 25 of models of cryostats that have various surface area configurations.

Referring to FIG. 3, an alternative embodiment of the present invention is illustrated, which employs 4 UV emitters 21 that will add to the surface coverage areas of the cryostat chamber 29 and microtome 25 of models of cryostats that have various surface area configurations. An alternative embodiment of the present invention may include 1 or more UV emitters 21 that can be adjusted in a way that will add to the surface coverage of the cryostat chamber 29 and microtome 25 of models of cryostats that have various surface area configurations.

Referring to FIG. 4, one method of operating the present invention is illustrated. In step 320, the UV emitters 21 are inserted into the cryostat chamber 29 via the cryostat chamber opening 28. In step 325, the mirrored cover 27 and UV shield 31 are closed over the cryostat chamber opening 28.

In step 330, the UV emission cycle is engaged, and the UV emitters 21 begin sending high intensity UV radiation to the surfaces of the cryostat chamber 29 and microtome 25.

In step 335, the UV waves strike the surfaces of the cryostat chamber 29 and microtome 25, breaking the organic molecular bonds of the microorganisms, which results in decontamination of the cryostat chamber 29.

In step 340, the cryostat disinfecting unit is removed from the cryostat chamber 29, and stored or used for decontamination of another cryostat.

Thus, it is seen that an apparatus and method for decontaminating a cryostat chamber using UV light are provided. One skilled in the art will appreciate that the present invention can be practiced by other than the preferred embodiments which are presented in this description for the purposes of illustration and not limitation and the present invention is limited only by the claims that follow. It is noted that the equivalents for the particular embodiments in this description may practice the invention as well.

What is claimed is:

1. A mobile ultraviolet light disinfection system comprising:
   at least one ultraviolet light emitter for disinfecting an interior of a cryostat, the cryostat defining a chamber having at least one side wall and a top opening;
   a pulsed power control system connected to the at least one emitter;
   whereby said at least one emitter will disinfect using said ultraviolet light; and
   a cover for positioning over the top opening, the cover carrying the at least one emitter whereby at least a portion thereof is held in the cryostat chamber interior when the cover is positioned over the top opening.

2. The disinfection system of claim 1, further comprising an ultraviolet light-protective shield for placing over the cover and an exterior of the cryostat.

3. The disinfection system of claim 1, wherein the cover includes a mirrored surface for reflecting ultraviolet light from the at least one emitter into the cryostat chamber interior.

4. The disinfection system of claim 1, wherein multiple emitters are used in an array.

5. The disinfection system of claim 1, wherein the at least one emitter generates ultraviolet energy in excess of 3 joules per square centimeter.

6. The disinfection system of claim 1, wherein the at least one emitter generates ultraviolet energy below 425 nanometers.

7. The disinfection system of claim 1, further comprising an emitter motion sequence.

8. The disinfection system of claim 1, further comprising a mirror motion sequence.

9. The disinfection system of claim 1, wherein any visible debris are first removed from the cryostat chamber with a biohazard filtered vacuum.

10. The disinfection system of claim 1, further comprising an adjustable timer control.

11. The disinfection system of claim 1, wherein the cover further includes stabilization bars for resting on a top of the at least one side wall of the cryostat.

12. The disinfection system of claim 11, further comprising a power cut-off switch which disables the at least one emitter when the cover is displaced from the top of the at least one side wall.

13. The disinfection system of claim 1, wherein the at least one emitter disinfects the cryostat chamber interior while said interior is in a low-temperature state.

14. A mobile ultraviolet light disinfection system comprising:
   at least one ultraviolet light emitter for disinfecting an interior of a cryostat defining a chamber having at least one side wall and a top opening;
   a pulsed power control system connected to the at least one emitter for causing emission of a sequence of pulses of high intensity ultraviolet light therefrom; and
   a cover for positioning over a top opening of the cryostat chamber, the cover carrying the at least one emitter whereby at least a portion thereof is held in the cryostat chamber interior when the cover is positioned over the top opening;
   the cover farther including a mirrored surface for reflecting ultraviolet light from the at least one emitter into the cryostat chamber interior.

15. The system of claim 14, wherein the cover further includes stabilization bars for resting on a top of the at least one side wall of the cryostat.

16. The system of claim 15, further including a power cut-off switch which disables the at least one emitter when the cover is displaced from the top of the at least one side wall.

17. The system of claim 14, further including an ultraviolet light-protective shield for placing over the cover and an exterior of the cryostat.

18. The system of claim 14, wherein the at least one emitter disinfects the cryostat chamber interior while said interior is in a low-temperature state.

19. A mobile ultraviolet light disinfection system comprising:
   at least two ultraviolet light emitters for disinfecting an interior of a cryostat defining a chamber having at least one side wall and a top opening, the cryostat further including a microtome positioned in said interior for supporting and cuffing a sample during use;
   a pulsed power control system connected to the at least two emitters for causing emission of a sequence of pulses of high intensity ultraviolet light therefrom to disinfect said chamber interior while said interior is in a low-temperature state; and
   a cover having a mirrored surface for positioning over a top opening of the cryostat chamber, the cover carrying the at least two emitters whereby at least a portion thereof is held in the cryostat chamber interior when the cover is positioned over the top opening;
   further wherein the at least two emitters are suspended whereby the microtome is positioned therebetween.

20. The system of claim 19, wherein the cover further includes stabilization bars for resting on a top of the at least one side wall of the cryostat.

21. The system of claim 19, further including a power cut-off switch which disables the at least two emitters when the cover is displaced from the top of the at least one side wall.

* * * * *